US010709869B2

(12) United States Patent
Basiony

(10) Patent No.: US 10,709,869 B2
(45) Date of Patent: Jul. 14, 2020

(54) RECIRCULATION MINIMIZING CATHETER

(71) Applicant: Mohamed A Basiony, Kenmore, WA (US)

(72) Inventor: Mohamed A Basiony, Kenmore, WA (US)

( * ) Notice: Subject to any disclaimer, the term of this patent is extended or adjusted under 35 U.S.C. 154(b) by 171 days.

(21) Appl. No.: 16/011,446

(22) Filed: Jun. 18, 2018

(65) Prior Publication Data

US 2019/0240451 A1 Aug. 8, 2019

Related U.S. Application Data

(60) Provisional application No. 62/626,064, filed on Feb. 3, 2018.

(51) Int. Cl.
*A61M 25/00* (2006.01)
*A61M 1/00* (2006.01)

(52) U.S. Cl.
CPC ...... *A61M 25/0071* (2013.01); *A61M 25/003* (2013.01); *A61M 25/007* (2013.01); *A61M 25/0041* (2013.01); *A61M 25/0097* (2013.01); *A61M 1/00* (2013.01); *A61M 2025/0031* (2013.01)

(58) Field of Classification Search
CPC ........... A61M 25/007; A61M 25/0026; A61M 25/003; A61M 25/0067; A61M 25/0071; A61M 25/0032; A61M 2025/0031
See application file for complete search history.

(56) References Cited

U.S. PATENT DOCUMENTS

2014/0018772 A1* 1/2014 Ash .................. A61M 25/0043 604/508
2014/0221898 A1* 8/2014 Kurrus ................ A61M 25/003 604/6.16

* cited by examiner

*Primary Examiner* — Matthew F Desanto

(57) ABSTRACT

A hemodialysis split-tip catheter comprises an elongated portion, a proximal end and a distal end defining a longitudinal axis. The proximal end attaches to a hub with suture wings assembly, which in turn connected to extension tubings. The distal end has two distal tip segments splitted from each other. The first distal tip segment has a concave shape with respect to the longitudinal axis and the second distal tip segment has an approximately J-shape with respect to first distal tip segment. Diameter of concave shape of first distal tip segment is larger than diameter of J-shape of second distal tip segment to facilitate backward bend of second distal tip segment with respect to first distal tip segment after a catheter insertion inside a blood vessel to face a blood flow direction.

5 Claims, 6 Drawing Sheets

14 27 26 22 28 12 13 15 15 25 10 24 21 23 10 29 30 32 31 20

RECIRCULATION MINIMIZING CATHETER

BACKGROUND

Catheterization may be required when a patient undergoes hemodialysis. A typical example of a hemodialysis catheter was a dual lumen catheter assembly in which one lumen introduced the blood and other lumen removed the blood.

Catheter performance during dialysis is a challenge, as use of catheters with higher recirculation, and/or suction, and/or occlusion issues results in adequate dialysis sessions. Adequate dialysis has been shown to be an independent predicator of increase hospitalization.

To specifically address the above issues, straight split-tip and curved split-tip catheters were designed to utilize independent "free floating" distal tip segments that separate at a distal end of the catheter to theoretically reduce likelihood of potential occlusion and sucking during dialysis treatment.

For recirculation issues, the prior art devices may have more than 20% of recirculation in a reverse blood lines configuration. Therefore, it would be desirable to provide a split-tip catheter that may minimize blood recirculation during dialysis in forward and reverse blood lines configurations.

SUMMARY

Accordingly, a hemodialysis split-tip catheter is described that may address blood recirculation issues. The catheter may comprise an elongated portion, a proximal end and a distal end defining a longitudinal axis. Said distal end may have two distal tip segments that may split (separated) from each other. A proximal end of such two distal tip segments may be coupled with a distal end of elongated portion.

First distal tip segment may have a concave shape with respect to longitudinal axis and a second distal tip segment may have an approximately J-shape with respect to first distal tip segment. A diameter of a concave shape of a first distal tip segment may be larger than a diameter of a J-shape of a second distal tip segment to may facilitate backward bend (curvature) of a second distal tip segment with respect to a first distal tip segment after a catheter insertion inside a blood vessel. This mechanism to may allow for a second distal tip opening of a second distal tip segment to face a blood flow direction.

Also, backward bend (curvature) of a second distal tip segment may increase a distance between two distal tip openings of both distal tip segments to be more than 30 mm to may more minimize a blood recirculation during dialysis sessions.

Elongated portion may have an exterior with generally round, oval or any other shapes in cross section. Also, elongated portion may have an internal longitudinally extending lumens of D-shape, or circular, or any other shapes. Each distal tip segment may have a D-shape, or circular, or any other shapes in cross section.

Proximal end of the catheter may attach to a hub with suture wings assembly, which in turn may be connected to extension tubings. Extension tubings may fluidly connect catheter lumens to a blood treatment unit or a dialysis machine.

BRIEF DESCRIPTION OF THE DRAWINGS

For the purpose of illustrating the disclosure, there are certain embodiments shown in the drawings of the present disclosure, however that the disclosure is not limited to the precise arrangements and instrumentalities shown. In the drawings, the same reference numbers are employed for designating the same elements throughout the several figures. In the drawings.

DETAILED DESCRIPTION

The following detailed description illustrates the principal of the disclosure by way of example not by way of limitation. While a reference use of the present disclosure describes a split-tip catheter to be used in hemodialysis, additional non-limiting usage would also include hemofiltration, hemodifiltration, blood adsorption, apheresis, as those of ordinary skill in the art will readily understand.

A hemodialysis split-tip catheter of present disclosure may be utilized as a short term or long term vascular access for above treatments and may be made by a biocompatible material like; polyethene, Silicon or any other suitable material. The catheter may also include an anti-microbial coating such as silver, methylene blue and the like. The catheter may be of any suitable size between 6 to 16 French circumferences, or any other suitable size.

The configuration of the catheter may be manipulated to facilitate placement of the catheter into a blood vessel. In one implementation, the catheter may be compressed into a substantially liner profile using a sheath. In an alternative implementation, the catheter may be placed over a guidewire (sheathless technique) with or without stylet to facilitate placement of the catheter into a blood vessel.

Figure 1:
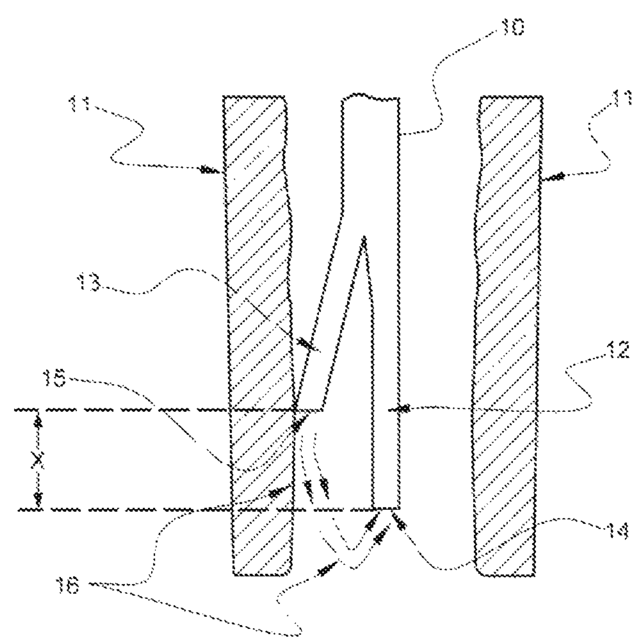
FIG. 1 illustrates a prior art typical split-tip catheter recirculating a blood from a second distal tip opening to a first distal tip opening during a reverse blood lines configuration according to the present disclosure.

FIG. 1 illustrates a prior art typical split-tip Catheter 10, a First Distal Tip Segment 12, a Second Distal Tip Segment 13 and a Blood Vessel Wall 11. First Distal Tip Segment 12 may have a First Distal Tip Opening 14 while a Second Distal Tip Segment 13 may have a Second Distal Tip Opening 15.

Still referring to FIG. 1, Arrows 16 represents a blood recirculation, in a reverse blood lines configuration, from a Second Distal Tip Opening 15 of a Second Distal Tip Segment 13 to a First Distal Tip Opening 14 of a First Distal Tip Segment 12, while "X" represents a distance between a First Distal Tip Opening 14 and a Second Distal Tip Opening 15.

Figure 2:
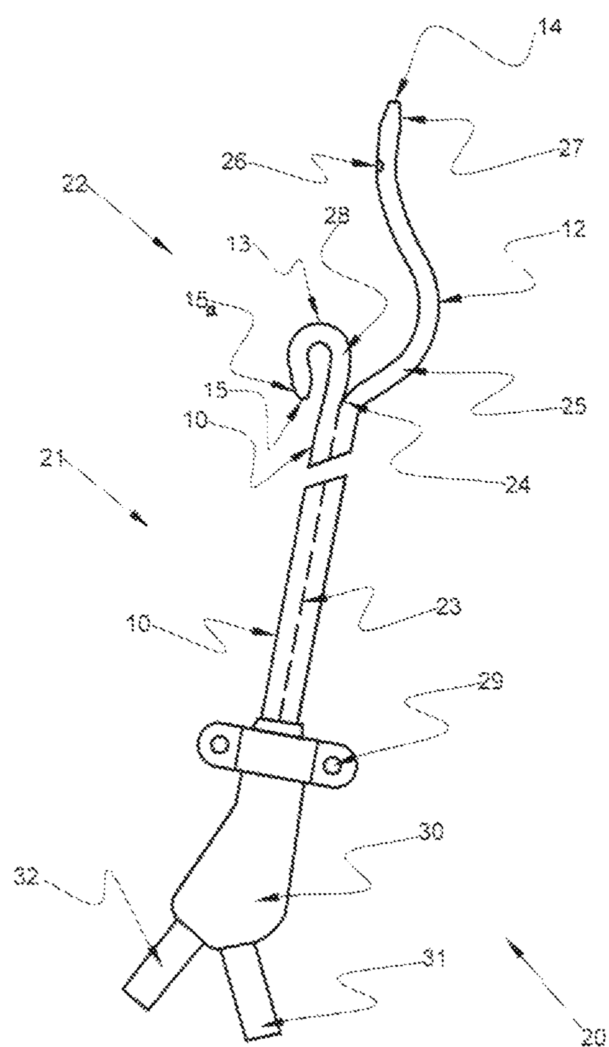
FIG. 2 is a perspective view of the hemodialysis split-tip catheter according to the present disclosure.

FIG. 2 illustrates a Catheter 20 that may include a Proximal End 21 and a Distal End 22 that may extend longitudinally to form an Elongated Portion (Catheter Body) 10. Elongated Portion (Catheter Body) 10 may be a straight or a pre-curved.

Proximal End 21 of a Catheter 20 may attach to a Hub 30 with Suture Wings Assembly 29, which in turn may be connected to Extension Tubings 31 and 32 as is standard in dialysis catheters. Extension Tubings 31 and 32 may fluidly connect Catheter Lumens 25 and 28 to a blood treatment unit or a dialysis machine (not shown for simplicity). 23 represents a Bisecting Planar Septum.

Distal End 22 of a Catheter 20 may splitted (separated) into a First Distal Tip Segment 12 and a Second Distal Tip Segment 13, distal to a Dividing Point 24. First Distal Tip Segment 12 may have a concave shape with respect to a longitudinal axis, Straight Tip 27 with a Side Hole 26 and a First Distal Tip Opening 14. Side Hole 26 may be used for a sheathless insertion technique and it may be a self-sealed.

Second Distal Tip Segment 13 may have approximately J-shape with respect to First Distal Tip Segment 12, a Distal Tip Opening 15 and a Tip 15*a*. Diameter of concave curvature of a First Distal Tip Segment 12 may be larger than a diameter of J-shape of a Second Distal Tip Segment 13 to may facilitate backward bend (curvature) of a Second Distal Tip Segment 13 with respect to a First Distal Tip Segment 12 after a Catheter 20 insertion inside a blood vessel.

Figure 3:
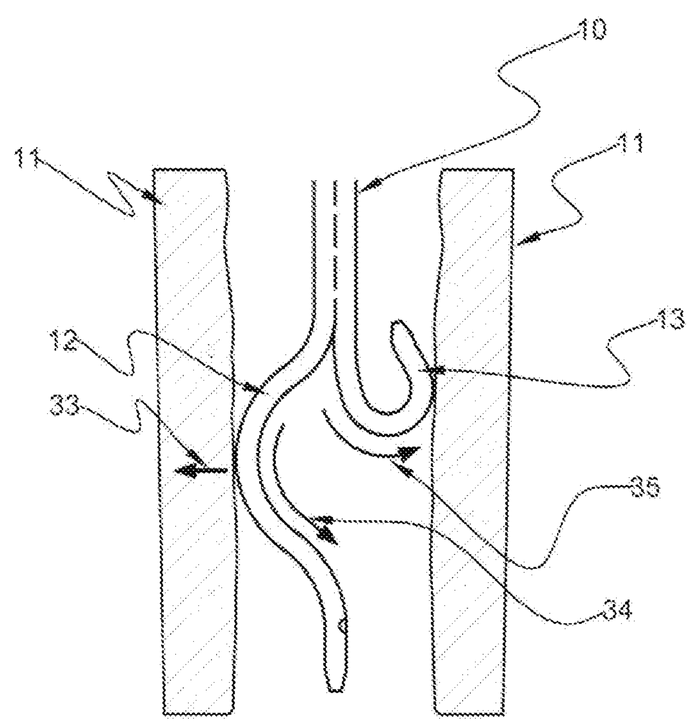
FIG. 3 illustrates how the first and second distal tip segments of the hemodialysis split-tip catheter of FIG. 2, restore their curvatures after insertion inside a blood vessel according to the present disclosure.

Referring now to FIG. 3 wherein an Elongated Portion (Catheter Body) 10, a Blood Vessel Wall 11 and First and Second Distal Tip Segments 12 and 13 respectively.

After insertion inside a blood vessel, a concave shape of a First Distal Tip Segment 12 may bend outwardly to restore its curvature shape as per Arrow 34, doing that it may push a Blood Vessel Wall 11 outwardly as indicated by Arrow 33 to enable a Second Distal Tip Segment 13 which may have a smaller diameter to restore its J-shape backwardly as per Arrow 35, with respect to a First Distal Tip Segment 12, to may face a blood flow direction.

Figure 4:
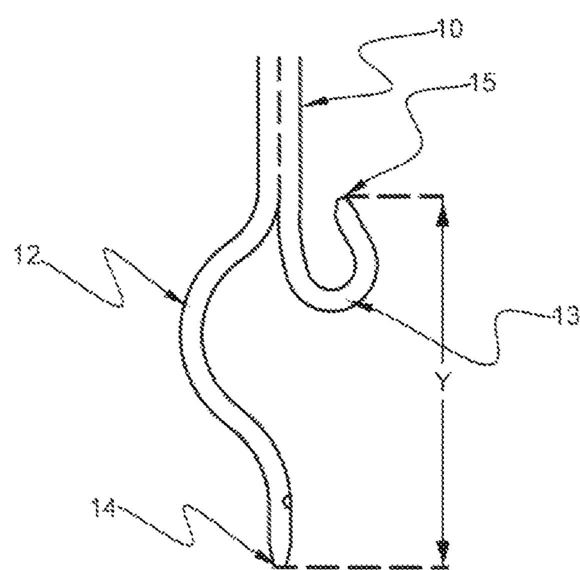
FIG. 4 illustrates the distance between a first distal tip opening of a first distal tip segment and a second distal tip opening of a second distal tip segment of the hemodialysis split-tip catheter of FIG. 2 according to the present disclosure.

Now referring to FIG. 4 wherein, an Elongated Portion (Catheter Body) 10, a First and a Second Distal Tip Segments 12 and 13 respectively, a First Distal Tip Opening 14 of a First Distal Tip Segment 12 and a Second Distal Tip Opening 15 of a Second Distal Tip Segment 13.

"Y" represents a distance between a First Distal Tip opening 14 of a First Distal Tip Segment 12 and a Second Distal Tip Opening 15 of a Second Distal Tip Segment 13. Due to backward bend of a Second Distal Tip Segment 13 (to form approximately J-shape), due to that configuration a Distance "X" in FIG. 1 is extended to a longer Distance "Y" as in FIG. 4.

In the prior art devices, a Distance "X" may have a maximum length of 30 mm. With the present disclosure, due to a backward bend of a Second Distal Tip Segment 13, a Distance "X" is extended to a Distance "Y" that may have a length more than 30 mm. The length "Y" may be about 30 mm to 70 mm or any other suitable lengths.

Figure 5A:
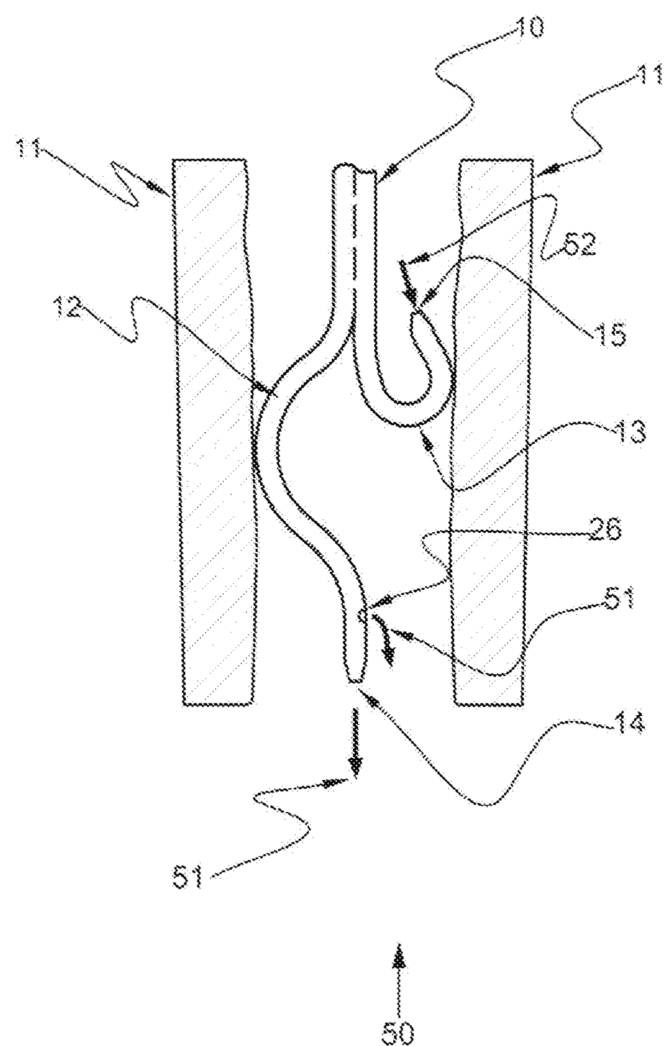
FIG. 5*a* illustrates direction of blood flow in a forward blood lines configuration of the hemodialysis split-tip catheter of FIG. 2 according to the present disclosure.

FIG. 5*a* illustrates inlet and outlet of blood in a Forward Blood Lines Configuration 50 wherein, an Elongated Portion (Catheter Body) 10, a Blood Vessel Wall 11, First and Second Distal Tip Segments 12 and 13 respectively. First Distal Tip Segment 12 may have a Side Hole 26 and a First Distal Tip Opening 14, while a Second Distal Tip Segment 13 may have a Second Distal Tip Opening 15.

Blood outlets from a First Distal Tip Opening 14 of a First Distal Tip Segment 12 and a Side Hole 26 (in case it may not be completely self-sealed) may be represented by Arrows 51 while a blood inlet to a Second Distal Tip Opening 15 of a Second Distal Tip Segment 13 may be represented by Arrow 52.

Figure 5B:
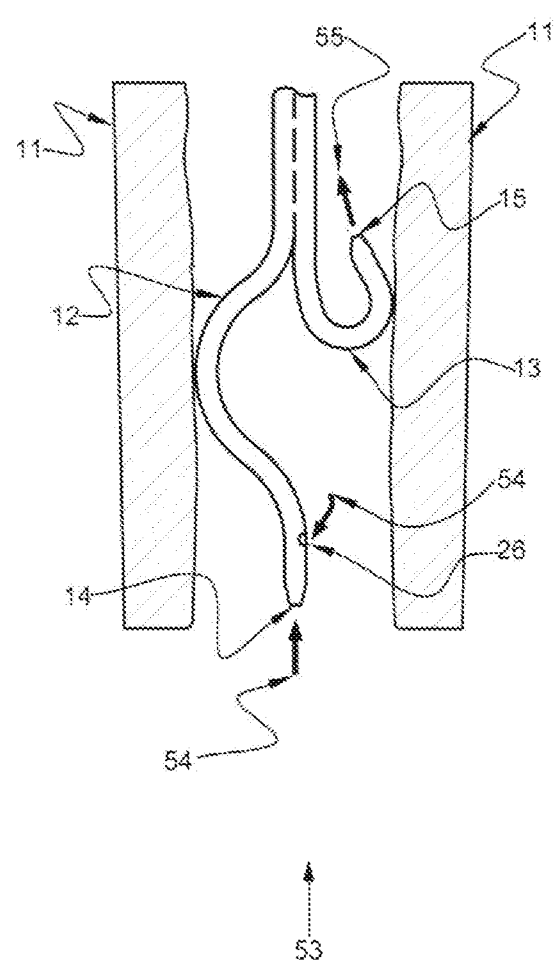
FIG. 5*b* illustrates direction of blood flow in a reverse blood lines configuration of the hemodialysis split-tip catheter of FIG. 2 according to the present disclosure.

FIG. 5*b* illustrates inlet and outlet of blood in a Reverse Blood Lines Configuration 53, wherein a Blood Vessel Wall 11, First and Second Distal Tip Segments 12 and 13 respectively. First Distal Tip Segment may have a Side Hole 26 and a First Distal Tip Opening 14, while a Second Distal Tip Segment 13 may have a Second Distal Tip Opening 15.

Blood inlet to a First Distal Tip Opening 14 and a Side Hole 26 (in case it may not be completely self-sealed) of a First Distal Tip Segment 12 may be represented by Arrows 54, while a blood outlet from a Second Distal Tip Opening 15 of a Second Distal End Segment 13, may be represented by Arrow 55.

Comparing FIG. 1, FIG. 4, FIG. 5*a* and FIG. 5*b* especially in a reverse blood lines configuration, those skilled in the art will recognize that backward bend of a Second Distal Tip Segment 13 with respect to a First Distal Tip Segment 12 may allow for a Second Distal Tip Opening 15 to may face a blood flow direction and also, extending a distance between a First Distal Tip Opening 14 of a First Distal Tip Segment 12 and a Second Distal Tip Opening 15 of a Second Distal Tip Segment 13, to be more than 30 mm, both steps may minimize a blood recirculation in a reverse blood lines configuration as well as in a forward blood lines configuration.

The invention claimed is:

1. A recirculation minimizing catheter comprising:

an elongated body portion having a longitudinal axis, a proximal end and a distal end;

the distal end comprising a first distal tip segment and a second distal tip segment that are split at a dividing point;

the first distal tip segment having a first lumen, a first distal tip, a straight tip with a side hole and a first distal tip opening;

the second distal tip segment having a second lumen, a second distal tip and a second distal tip opening, wherein the second distal tip segment is configured to have a J-shape with respect to the first distal tip segment;

the first distal tip segment having a concave shape with respect to the longitudinal axis, having a diameter of curvature that is larger than a diameter of curvature of the second distal tip segment, the first distal tip segment and the second distal tip segment each have a contact point that is configured to engage a blood vessel wall, and the first distal tip opening and the second distal tip opening have a distance between the two distal tip openings with a length more than 30 mm; and wherein the recirculation minimizing catheter is configured such that the first distal tip segment after insertion inside a blood vessel bends outwardly and pushes the blood vessel wall outwardly to facilitate the bend backwardly of the second distal segment to form the j-shape to face a blood direction in the blood vessel.

2. The recirculation minimizing catheter of claim 1 wherein the backwardly bend of the second distal tip segment is arranged to minimize a blood recirculation via extending the distance between the distal tip opening of the first distal tip segment and the distal tip opening of the second distal tip segment.

3. The recirculation minimizing catheter of claim 1 wherein the first distal tip opening of the first distal tip segment is at a distal configuration relative to the J-shaped configuration of the second distal tip segment.

4. The recirculation minimizing catheter of claim 1 wherein in a forward blood lines configuration, the recirculation minimizing catheter is configured to have a blood outlet at the first distal tip opening and a blood inlet at the second distal tip opening, wherein the flow of the blood is in the same direction.

5. The recirculation minimizing catheter of claim 1 wherein in a reverse blood lines configuration, the recirculation minimizing catheter is configured to have a blood inlet at the first distal tip opening and a blood outlet at the second distal tip opening, wherein the flow of the blood is in the same direction.

* * * * *